United States Patent [19]

Fox et al.

[11] Patent Number: 5,738,646
[45] Date of Patent: *Apr. 14, 1998

[54] THERMOPLASTIC APPLICATOR EXHIBITING ACCELERATED BREAKUP WHEN IMMERSED IN WATER

[75] Inventors: Donald George Fox, Neenah; Daniel James Heuer, Larsen; Frederick Myron Guenther, Oshkosh, all of Wis.

[73] Assignee: Kimberly-Clark Worldwide, Inc., Neenah, Wis.

[*] Notice: The term of this patent shall not extend beyond the expiration date of Pat. No. 5,395,308.

[21] Appl. No.: 381,007

[22] Filed: Jan. 30, 1995

Related U.S. Application Data

[63] Continuation of Ser. No. 126,465, Sep. 24, 1993, Pat. No. 5,395,308.
[51] Int. Cl.$^6$ .................................................. A61F 13/20
[52] U.S. Cl. ........................... 604/15; 604/11; 604/14
[58] Field of Search ............................... 604/11–18, 288

[56] References Cited

U.S. PATENT DOCUMENTS

| | | |
|---|---|---|
| 2,489,502 | 11/1949 | Ruth . |
| 3,433,225 | 3/1969 | Voss et al. . |
| 3,696,812 | 10/1972 | Jaycox . |
| 3,717,149 | 2/1973 | Morane . |
| 3,881,487 | 5/1975 | Schrading . |
| 4,198,978 | 4/1980 | Nigro . |
| 4,271,835 | 6/1981 | Conn et al. . |
| 4,412,833 | 11/1983 | Wiegner et al. . |
| 4,453,925 | 6/1984 | Decker . |
| 4,508,531 | 4/1985 | Whitehead . |
| 5,002,526 | 3/1991 | Herring . |
| 5,087,239 | 2/1992 | Beastall et al. . |
| 5,158,535 | 10/1992 | Paul et al. . |
| 5,389,068 | 2/1995 | Keck .................................. 604/15 |
| 5,395,308 | 3/1995 | Fox et al. ........................... 604/15 |

FOREIGN PATENT DOCUMENTS

| | | |
|---|---|---|
| 0243250 | 10/1987 | European Pat. Off. . |
| 777411 | 12/1977 | South Africa . |
| 2114448 | 8/1983 | United Kingdom . |
| 2132484 | 7/1984 | United Kingdom . |
| 2133695 | 8/1984 | United Kingdom . |

*Primary Examiner*—John G. Weiss
*Assistant Examiner*—Dennis Ruhl
*Attorney, Agent, or Firm*—Thomas J. Connelly

[57] ABSTRACT

A thermoplastic applicator is disclosed which exhibits accelerated breakup when immersed in water. The applicator includes a hollow, cylindrically shaped member which holds a pledget. This cylindrically shaped member is constructed of a water-soluble or water-dispersible material and has a wall with a thickness of less than about 0.05 inches (about 12.7 mm). A plurality of grooves are formed in the wall in a predetermined pattern to accelerate breakup of the applicator into small unrecognizable pieces. The grooves have a depth of between about 5 percent to 75 percent of the thickness of the wall. The deeper the grooves, the shorter the time period needed to breakup the applicator.

22 Claims, 3 Drawing Sheets

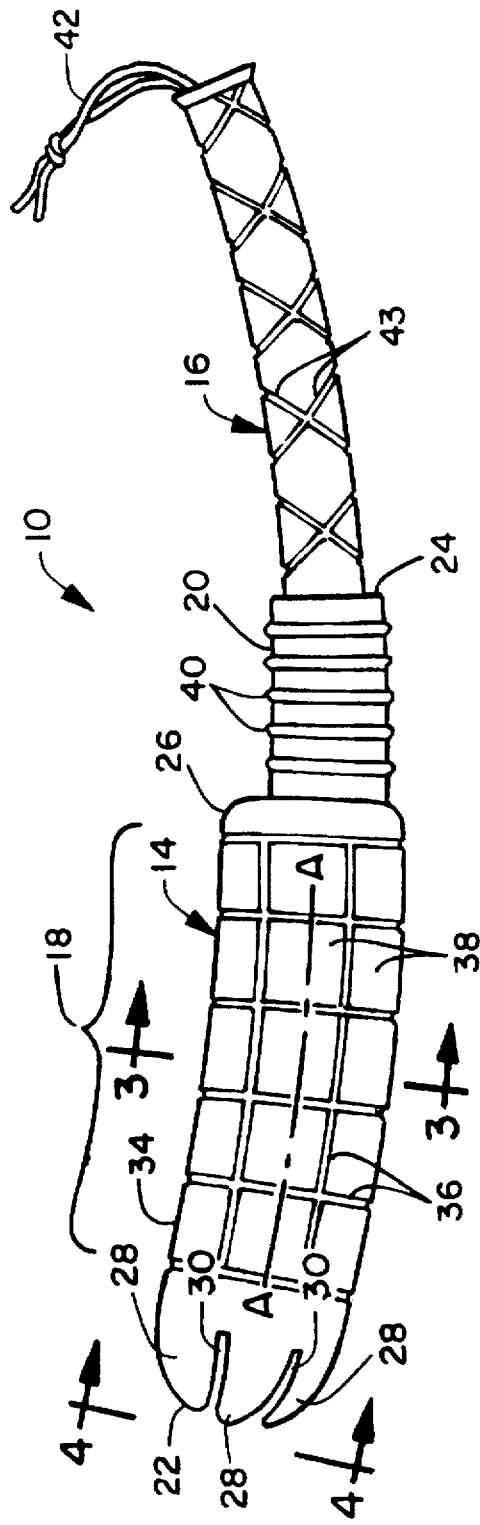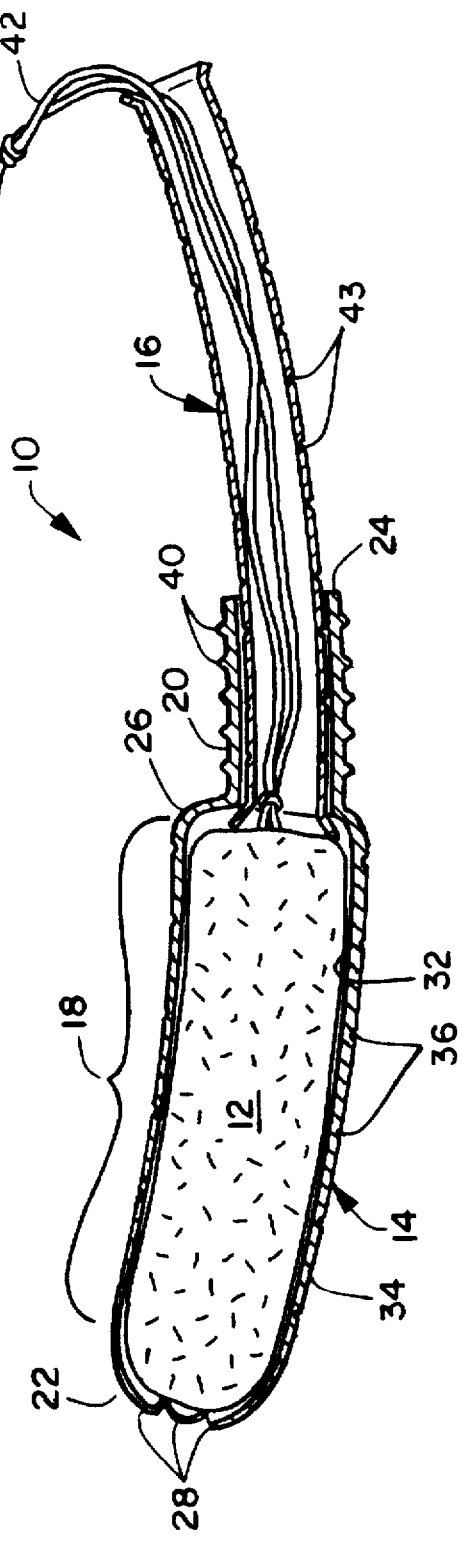

1

THERMOPLASTIC APPLICATOR EXHIBITING ACCELERATED BREAKUP WHEN IMMERSED IN WATER

This is a continuation of copending application Ser. No. 08/126,465, filed on Sep. 24, 1993, now U.S. Pat. No. 5,395,308.

FIELD OF THE INVENTION

This invention relates to a thermoplastic applicator having a plurality of grooves formed in the walls thereof in a predetermined pattern to accelerate breakup of the applicator when the applicator is immersed in water.

BACKGROUND OF THE INVENTION

Applicators for hygienic purposes, such as catamenial tampons, suppository devices, medicament applicators for humans and animals, and the like, are utilized daily in large quantities. Such applicators are manufactured in a variety of shapes and sizes and can be constructed out of different materials. For tampon applicators in particular, the materials can include plain paper, coated paper, cardboard, injection molded and extrusion molded thermoplastics, and thermoplastic films. Some of these materials are biodegradable, photodegradable, ultraviolet light degradable, water soluble, water dispersible or compostable, at least to a certain degree. The disposal of such applicators can present an environmental issue if it does not occur quickly and completely.

In the past, many applicators, especially tampon applicators, were constructed out of paper held together by water-soluble glues. When such applicators were disposed of by flushing them down a toilet, the applicator would readily break apart in the water and become unrecognizable. With the advent of plastic applicators and paper applicators coated with a thermoplastic film, manufactures and water-treatment plant operators in particular, have become aware that many of such applicators do not dissolve or degrade sufficiently within a reasonable period of time. Even applicators made from water-dispersible and/or water-soluble resins can require an extended time period before they break apart or substantially dissolve. The differences in breakup time can be attributed to the chemical composition of the plastic, the applicator design and shape, varying wall thicknesses, the water temperature in which the applicators are immersed, the amount of agitation the applicators may be exposed to, etc.

It has been found by experimentation that many thermoplastic applicators, which are water-soluble, tend to collapse into a sticky glob of plastic. While the plastic is unrecognizable as a tampon applicator, the plastic can still clog up the filtration system of a municipality's sewage and waste treatment plant. This is undesirable today and there is a need to design and manufacture applicators made from thermoplastic applicators and paper applicators coated with a thermoplastic material which can breakup into small pieces very quickly, especially in cold water. Once the applicator has broken apart, the individual pieces can dissolve over an extended period of time without causing problems in the waste treatment facilities.

Now a thermoplastic, water-dispersible applicator has been invented which exhibits accelerated breakup into small pieces when the applicator is immersed in water.

SUMMARY OF THE INVENTION

Briefly, this invention relates to an applicator for hygienic purposes, such as catamenial tampons, suppository devices, medicament applicators for humans and animals, and the like. Applicators, especially tampon applicators, facilitate the insertion of a pledget into a body cavity. The pledget can be an absorbent article or it can be a carrier for medication which can be conveyed to a particular area of the body.

The applicator includes a hollow, cylindrically shaped thermoplastic member which holds a pledget. This member is constructed of a water-dispersible material having a wall with a thickness of less than about 0.05 inches (1.27 mm). A plurality of grooves are formed in the wall during manufacture, in a predetermined pattern, to accelerate breakup of the applicator when the applicator is immersed in water. The grooves have a depth of between about 5 percent to 75 percent of the thickness of the wall. The deeper the grooves, the shorter the time period needed to break apart the applicator into small pieces.

The general object of this invention is to provide a thermoplastic applicator exhibiting accelerated breakup when immersed in water. A more specific object of this invention is to provide a thermoplastic tampon applicator having a pattern of grooves formed therein which exhibits accelerated breakup of the applicator when the applicator is immersed in water.

Another object of this invention is to provide a thermoplastic, water-dispersible applicator which has a plurality of thin areas located between adjacent wall sections for accelerating breakup of the applicator when the applicator is immersed in water.

A further object of this invention is to provide a curved tampon applicator having a decorative pattern formed in the outer periphery thereof which provides a pleasing aesthetic appearance as well as providing a means for allowing the applicator to rapidly disintegrate in a liquid, such as water.

Still another object of this invention is to provide a thermoplastic, water-dispersible applicator which can be injection molded or extrusion molded.

Still further, an object of this invention is to provide a thermoplastic, water-dispersible applicator which is relatively inexpensive to manufacture.

Other objects and advantages of the present invention will become more apparent to those skilled in the art in view of the following description and the accompanying drawings.

BRIEF DESCRIPTION OF THE DRAWINGS

FIG. 1 is a side elevation view of an applicator having a plurality of grooves formed in a pattern on the outer periphery thereof.

FIG. 2 is a cross-sectional view of the applicator shown in FIG. 1 depicting an absorbent tampon positioned in the cylindrically shaped outer member.

DETAILED DESCRIPTION OF THE PREFERRED EMBODIMENTS

Figure 3:
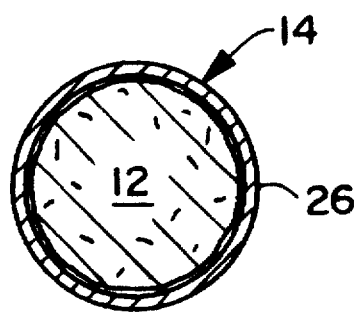
FIG. 3 is a cross-sectional view of the applicator taken along line 3—3 of FIG. 1.

Referring to FIGS. 1 and 2, a hygienic applicator 10 is shown for inserting an absorbent and/or medicinal media into an appropriate body cavity. The applicator 10 is depicted for purposes of discussion only, as a catamenial applicator containing an absorbent pledget 12. It should be noted that the applicator 10 could be any type of applicator useful for hygienic purposes. In the case of a tampon applicator, the pledget 12 is intended to be inserted into a woman's vagina during her menstrual period to block and absorb the flow of menstrual fluid, blood, etc. therefrom.

The applicator 10 includes a first member 14 and a second member 16. The first member 14 is a hollow, elongated, cylindrically shaped member having a length of about 2 inches to 3 inches (about 50.8 mm to 76.2 mm) and a diameter of about ¼ inch to 1 inch (about 6.35 mm to 25.4 mm). It should be noted that although the first member 14 is described as having a circular or round cross-section, that a square, rectangular, elliptical, oval or other configuration could also be used.

The first member 14 is constructed out of a thermoplastic material which should be capable of being injected or extrusion molded. The thermoplastic material can be clear or opaque.

The thermoplastic material should be water dispersible and preferably, water soluble. The thermoplastic material could also be photodegradable, ultraviolet light degradable, biodegradable or compostable. Various types of thermoplastics resins and miscible blends thereof can be used. The applicator 10 should be flushable in conventional toilet systems and be capable of breaking apart in water maintained above, at or below room temperature.

The thermoplastic material can be made from a polyester containing an ionic metal salt substituent. This material and variations thereof are taught in patent application U.S. Ser. No. 07/938,963 which is incorporated by reference and made a part hereof. Another thermoplastic material which works well is made from blends of a linear, water-dissipatable polymer having ethylene oxide groups in the linear molecular structure. The blend can include polyethylene co-vinyl alcohol, polycaprolactone, Nylon 11, Nylon 12, polyvinyl acetate, polyethylene co-vinyl acetate, polyethylene co-methacrylic acid, polyethylene co-acrylic acid, polyvinyl chloride, polystyrene, polymethyl methacrylate, or polystyrene co-methyl methacrylate.

Still other thermoplastic materials which can be utilized are thermoplastics compounded from linear, thermoplastic polyethylene oxide blended with a thermoplastic polymer.

Lastly, the thermoplastic materials can be a resin or a coating made from low density polyethylene, polyvinyl alcohol, polyethylene oxide, polyvinyl acetate, polyvinyl pyrolidone or hydroxypropyl cellulose.

The first member 14 can be straight or curved but is depicted in some of the drawings as having an arcuate shape with a centerline A—A formed on an arc having a predetermined radius of curvature. The arc can be formed with a radius of curvature of between about 6 inches to 10 inches (about 152.4 mm to 254 mm), preferably between about 7 inches to 9 inches (about 177.8 mm to 228.6 mm), and most preferably, about 8 inches (203.2 mm). An arc having a certain radius of curvature is equivalent to an arcuate segment of a circle having a given radius.

Referring again to FIGS. 1–3, the first member 14 has a stepped outer configuration with an enlarged, cylindrically shaped portion 18, designed to hold the pledger 12, joined to a smaller finger grip portion 20. The first member 14 also has first and second, spaced apart ends 22 and 24, respectively. The first or expulsion end 22 is the end from which the pledget 12 is removed from the applicator 10 and the second or opposite end 24 is adjacent to the finger grip portion 20. The cylindrically shaped portion 18 is hollow and is sized to be slightly larger than the outside diameter of the pledget 12, which it is designed to house. The cylindrically shaped portion 18 is constructed with a wall 26 which can be either uniform or variable in thickness.

In FIG. 2, the wall 26 is shown having a taper wherein it is thicker approximate the second end 24 and narrows as it approaches the first end 22. The wall 26 can be thin having a thickness of less than about 0.05 inches (about 1.3 mm), preferably less than about 0.03 inches (about 0.76 mm), and more preferably, from about 0.005 inches to 0.025 inches (about 0.127 mm to 0.635 mm). The exact thickness and the amount of taper in the wall 26 will depend upon the size of the applicator 10, the material from which the applicator 10 is manufactured, the application for which the applicator 10 is designed to be used, as well as other factors known to those skilled in the art.

Figure 4:
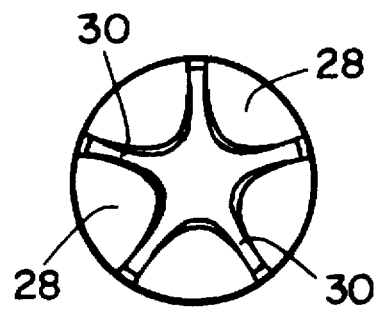
FIG. 4 is an end view of the cylindrically shaped member taken along line 4—4 of FIG. 1.

Referring to FIGS. 1 and 4, a plurality of thin, flexible petals 28 are formed at the first end 22 of the wall 26 to form a dome shaped nose. The petals 28 are separated by slots 30. The petals 28 are capable of radially flexing or bending outward to enable the pledget 12 to be expelled from the first member 14. The petals 28 are preferably arranged in an odd number, such as 3, 5, 7, etc. because an odd number of petals 28 will prevent the first member 14 from collapsing or flattening after the pledget 12 has been expelled. By preventing the first member 14 from collapsing, one can be assured that the vaginal tissue, in the case of a tampon applicator, will not be pinched when the applicator 10 is removed. For optimum performance, a tampon applicator will have five petals 28, each having an elongated triangular shape and being about 7/16 of an inch (about 11.1 mm) long.

Referring again to FIGS. 1 and 2, the cylindrically shaped portion 18 of the first member 14 has an inner and an outer periphery, 32 and 34 respectively, formed by the wall 26. Formed or cut into the surface of the outer periphery 34 are a plurality of grooves 36. By "groove" is meant a thin area having a width less than or equal to the land area adjoining it. The grooves 36 can have a width of less than about 1 mm., preferably less than about 0.1 mm, and most preferably, less than about 0.01 mm. The grooves 36 serve to enable the applicator 10 to exhibit accelerated breakup of the wall 26 when the applicator 10 is immersed in water. The grooves 36 can completely or partially surround the circumference of the outer periphery and have a depth ranging from about 5% to 75% of the thickness of the wall 26. Preferably, the grooves 36 have a depth of about 25% to 75% of the wall thickness, more preferably, about 25% to 50% of the wall thickness, and most preferably, about 30% of the wall thickness. Good breakup can be obtained when the depth of the grooves 36 is equal to approximately half of the wall thickness in the section of the applicator in which the grooves 36 are formed.

The depth of an individual groove 36 can vary over it's length and the depth of a groove 36 can be different from the depth of other grooves if desired. The exact depth of a groove 36 will be dictated by the composition of the thermoplastic material, as well as the time interval in which the applicator 10 is designed to break apart and the liquid medium in which the applicator 10 will disperse. A desirable time interval is under 15 minutes, preferably under 10 minutes, and most preferably, under 5 minutes. The time required to break apart the applicator can be much shorter than the time required to totally dissolve all of the thermoplastic material.

It is desirable to form the grooves 36 into the applicator 10 during the injection molding or extrusion molding process. However, the grooves 36 could be cut or embossed into the surface of the applicator 10 after it is formed, such as with a knife. When injection molding, the male portions of the mold designed to form the grooves 36 should be built with enough clearance or draft to enable the moving parts of the mold to open and close without interference.

The grooves 36 can be continuous or discontinuous and can be either linear or nonlinear in configuration. The grooves 36 can be arranged at any angle within the first member 14. The grooves 36 can have a U-shaped, V-shaped, tapered or other type of cross-sectional configuration and should be sized relative to the thickness of the wall 26 and in contemplation of the length of time required before the wall 26 is suppose to break apart. Because the intent of the grooves 36 is to accelerate the break up of the wall 26 into smaller segments, it is advantageous to arrange the grooves 36 such that at least one of the grooves 36 will intersect, cross, or contact another groove 36. Such intersections and/or contact points should occur at least every ½ inch (about 12.7 mm). Preferably, such intersections and/or contact points will occur about every ¼ inch (about 6.35 mm). A contact point can be an angular joint formed between two or more grooves 36. For example, one of the T-shaped joints depicted in FIGS. 1 and 2 would be a contact point. By "T-shape joint" is meant a location where a first groove 36 perpendicularly joins a second groove 36 without crossing over the second groove. It should be noted that if two or more grooves 36 do not actually contact or cross one another but are arranged in close proximity to one another, that the same desirable effect of enabling accelerated break up of the applicator 10 can be realized.

As shown in FIGS. 1 and 2, the grooves 36 are only formed in the cylindrically shaped portion 18 of the first member 14. However, if desired, the grooves 36 could also be formed in the petals 28 and/or in the finger grip portion 20. It should be recognized that it is advantageous to keep the outer surface of the petals 28 smooth so that they do not pinch or scratch the vaginal tissue during insertion of the applicator 10.

In FIGS. 1 and 2, the grooves 36 are arranged in a grid-shaped pattern wherein the grooves 36 are aligned parallel or perpendicular to one another. By "grid-shaped" it is meant a framework of parallel and perpendicular lines. A plurality of crisscrossed bars established by horizontal and vertical grooves 36 will form wall segments 38, for example squares of uniform or varying size. The small thermoplastic wall segments 38, located between the intersecting grooves 36, establish the size and shape of the material which will temporarily remain once the material under the grooves 36 dissolves or breaks away. As such, the small segments 38 should have a length, width or diameter no larger than about 0.5 inches (about 12.7 mm). This size wall segment 38 will not cause problems in the filtration system of most municipal waste treatment plants, should the wall thickness be such that additional time is required before the thermoplastic applicator totally dissolves or breaks apart.

The tampon applicator 10 shown in FIGS. 1 and 2 also has a finger grip portion 20 which is greater in thickness than the first member 14. The reason for this is that the finger grip portion 20 has to be rigid enough to retain the second member 16. The second member 16 or plunger, as it is sometimes referred to, is hollow having a thin wall and is open at each end. The second member 16 is slidable and telescopically mounted within the finger grip portion 20 so as to be able to expel the pledget 12 from the first member 14 once the cylindrically shaped portion 18 is inserted into a woman's vagina. The second member 16 can have an oval or elliptical cross-section to prevent it from rotating within the finger grip portion 20.

The finger grip portion 20 can be formed with one or more ribs or protrusions 40 on it's exterior to provide a gripping surface to assist the user in holding the applicator 10. Other types of gripping means can also be used, such as score lines, ridges, rings, dimples, one or more flat surfaces, a roughened surface, etc. It should be noted that after the tampon pledget 12 is inserted into the vagina, the applicator 10 can be disposed of by flushing it down a toilet. A withdrawal string 42 is permanently attached to one end of the pledget 12 and provides a means for withdrawing the soiled tampon pledget 12 from the vagina. It should also be noted that the second member 16 can also contain one or more grooves 43 formed in it's inner or outer periphery which would serve the same purpose as the grooves 36 which are formed in the first member 14. Preferably, the grooves 43 are formed in a pattern as was explained above relative to the first member 14. Another alternative available to manufacturers is to form the second member 16 out of a thermoplastic material which can dissolve or break apart quicker than the first member 14.

Figure 5:
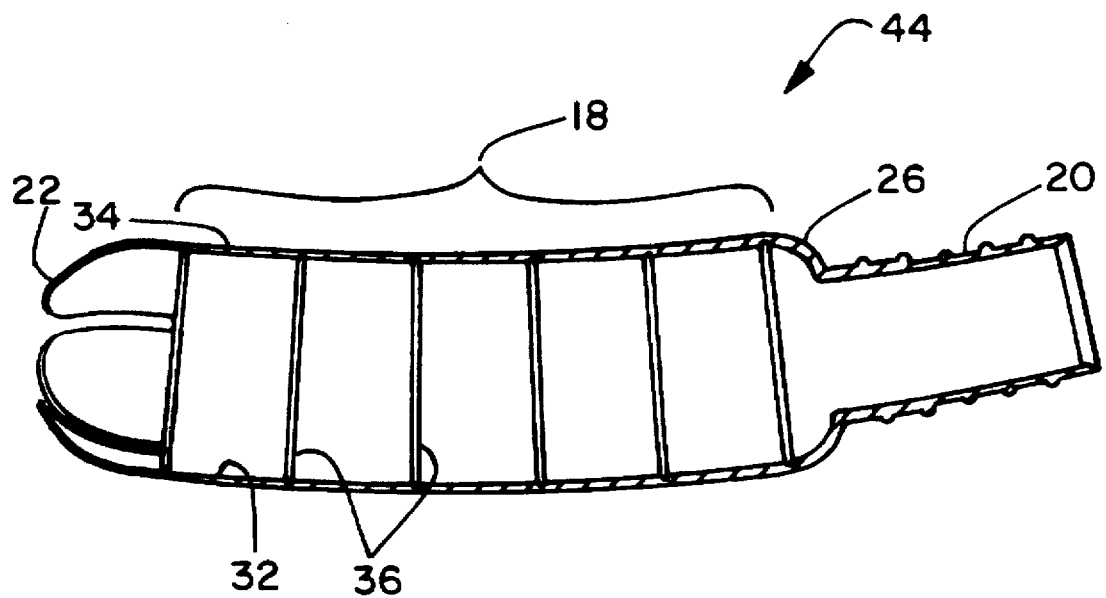
FIG. 5 is a cross-sectional view of an applicator having a plurality of grooves formed in a pattern on the inner periphery thereof.

Referring to FIG. 5, a first member 44 of an applicator is shown which is identical to the first member 14 shown in FIG. 1 except that a plurality of grooves 36 are formed on the inner periphery 32 instead of on the outer periphery 34. When the grooves 36 are formed on the inner periphery, the material above the groove lines will break apart when the applicator is immersed in water. By forming the grooves 36 on the inner periphery, the outer periphery can remain smooth and the consumer may not even be aware that the grooves 36 are present. This is desirable in those applications where a smooth outer surface is necessary. It should also be noted that the grooves 36 can be formed on both the inner and outer peripheries, 32 and 34 respectively, (not shown) if desired.

Figure 6:
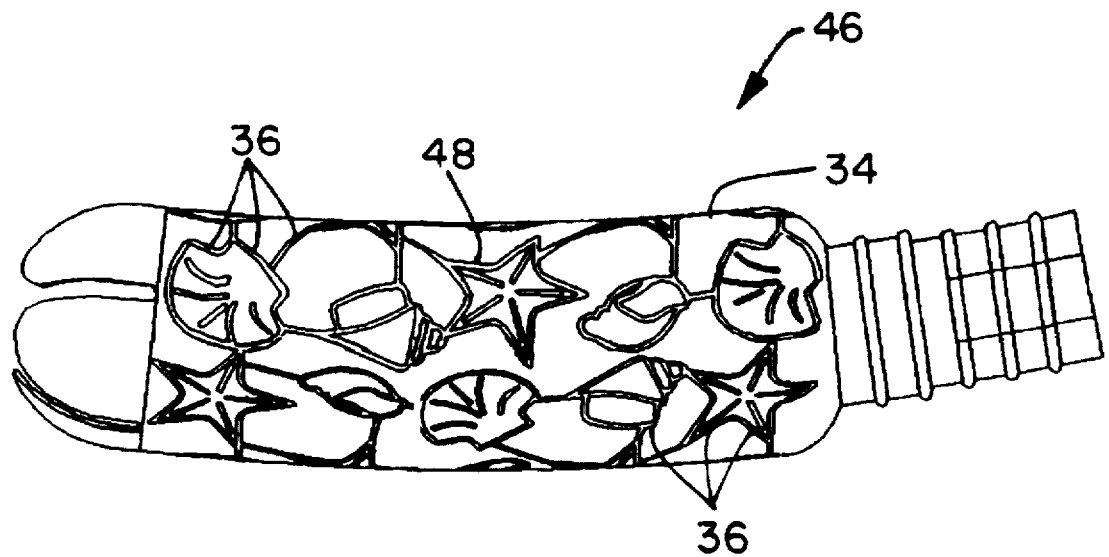
FIG. 6 is a side elevation view of an applicator having a plurality of grooves forming a decorative sea shell pattern in the outer periphery thereof which accelerates breakup of the applicator when the applicator is immersed in water.

Referring to FIG. 6, a first member 46 of an applicator is shown wherein a decorative sea shell pattern 48 is present on the outer periphery 34 by arranging the grooves 36 in a unique fashion. Other decorative designs can also be obtained by using continuous and/or discontinuous groove lines. The decorative designs can add to the aesthetic appearance of the applicator 10 and increase the sales of such products.

Figure 7:
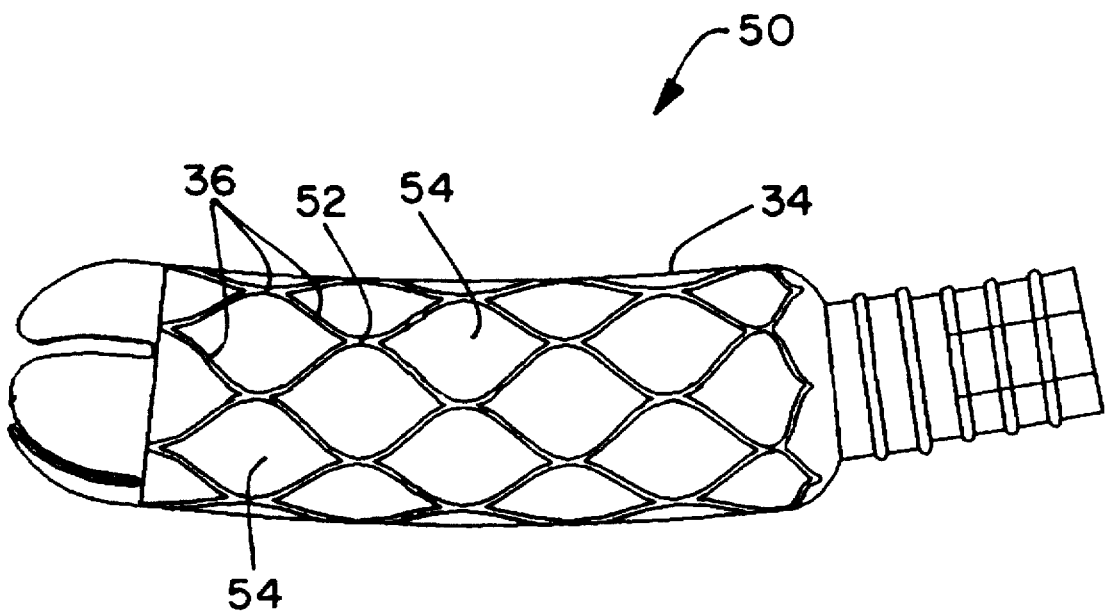
FIG. 7 is a side elevation view of an applicator having a plurality of grooves forming a decorative acorn pattern in the outer periphery thereof which accelerates breakup of the applicator when the applicator is immersed in water.

Referring to FIG. 7, a first member 50 of an applicator is shown wherein a decorative acorn-shaped pattern 52 is present on the outer periphery 34 by arranging the grooves 36 in a unique fashion. By "acorn-shaped" pattern is meant a pattern consisting of a string of acorn shaped segments 54. The acorn-shaped pattern 52, like the grid-shaped pattern shown in FIG. 1, provides approximately equal sized segments 54 once the first member 50 breaks up at the grooves 36. The presence of approximately equal size segments 54 particles can be advantageous in that experiments can be conducted to find out how long such size segments require to totally dissolve. This data can be matched with the holding time in the waste treatment facility such that the thermoplastic material will be either totally dissolved or unrecognizable before it is discharged into a river, lake, ocean or landfill.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An applicator comprising:
   a) a first member designed to hold a pledget, said member being constructed of a thermoplastic, water-dispersible material and having a thin wall, said member having an inner and an outer periphery; and
   b) a plurality of grooves formed in said wall for accelerating breakup of said first member when said applicator is immersed in water, said grooves having a depth of between about 5%–75% of said wall thickness.

2. The applicator of claim 1 wherein said grooves have a depth of between about 25%–75% of said wall thickness.

3. The applicator of claim 2 wherein said grooves have a depth of between about 25%–50% of said wall thickness.

4. The applicator of claim 1 wherein said grooves form a decorative pattern on said outer periphery of said first member.

5. The applicator of claim 1 wherein said grooves form a pattern on said inner periphery of said first member.

6. The applicator of claim 1 wherein at least some of said grooves are continuous.

7. The applicator of claim 1 wherein at least some of said grooves are discontinuous.

8. The applicator of claim 1 wherein at least one of said grooves is intersected by another of said grooves.

9. The applicator of claim 1 wherein said grooves are formed into said wall when said applicator is injected molded.

10. A tampon applicator comprising:
    a) a hollow, cylindrically shaped member designed to hold a tampon which is constructed of a thermoplastic, water-dispersible material, said member having a wall with a thickness of less than 0.05 inches, and said member having an inner and an outer periphery; and
    b) a plurality of grooves formed in said wall for accelerating breakup of said wall when said member is immersed in water, said grooves having a depth of between about 5%–75% of said wall thickness, and said grooves forming a pattern wherein a plurality of said grooves joins up with at least one other groove approximately every 0.5 inches.

11. The applicator of claim 10 wherein at least one of said grooves is intersected by another of said grooves.

12. The applicator of claim 11 wherein a plurality of said grooves intersect at least one other groove.

13. The applicator of claim 10 wherein said cylindrically shaped member has an outer periphery and said grooves form a decorative pattern in said outer periphery.

14. A tampon applicator comprising:
    a) a hollow, cylindrically shaped member constructed of a thermoplastic, water-dispersible material which is capable of holding a pledget, said member having an expulsion end which contains a plurality of petals and an opposite end which contains a finger grip, said petals capable of radially flexing outward to enable said pledget to be expelled from said member, and said member having a wall with a thickness intermediate said ends of less than about 0.05 inches;
    b) a plunger telescopically mounted in said cylindrically shaped member, said plunger adapted to expel said pledget through said expulsion end; and
    c) a plurality of grooves formed in said wall of said cylindrically shaped member intermediate said ends, said grooves accelerating breakup of said member when said applicator is immersed in water, said grooves having a depth of between about 5%–75% of said wall thickness.

15. The applicator of claim 14 wherein said grooves have a depth of between about 25%–75% of said wall thickness.

16. The applicator of claim 14 wherein said plunger is hollow having a thin wall and a plurality of grooves are formed in said wall for accelerating breakup of said plunger when said applicator is immersed in water.

17. The applicator of claim 14 wherein said cylindrically shaped member has an outer periphery and said grooves form a grid-shaped pattern in said outer periphery.

18. The applicator of claim 14 wherein said cylindrically shaped member has an inner periphery and said grooves form a grid-shaped pattern in said inner periphery.

19. The applicator of claim 14 wherein said cylindrically shaped member has an outer periphery and said grooves form a decorative pattern in said outer periphery.

20. The applicator of claim 14 wherein said cylindrically shaped member has an inner periphery and said grooves form a decorative pattern in said inner periphery.

21. The applicator of claim 14 wherein at least one of said grooves has a V-shaped cross-section.

22. The applicator of claim 14 wherein at least one of said grooves has a U-shaped cross-section.

* * * * *